(12) United States Patent
Savage et al.

(10) Patent No.: US 7,708,959 B2
(45) Date of Patent: May 4, 2010

(54) STERILIZATION SYSTEM AND METHOD SUITABLE FOR USE IN ASSOCIATION WITH FILLER DEVICES

(75) Inventors: Chester Savage, Irvine, CA (US); Douglas K. Stricklin, Brea, CA (US)

(73) Assignee: Scholle Corporation, Irvine, CA (US)

( * ) Notice: Subject to any disclaimer, the term of this patent is extended or adjusted under 35 U.S.C. 154(b) by 872 days.

(21) Appl. No.: 11/489,834

(22) Filed: Jul. 20, 2006

(65) Prior Publication Data
US 2008/0019864 A1    Jan. 24, 2008

(51) Int. Cl.
*A61L 2/00* (2006.01)
*B65B 55/04* (2006.01)

(52) U.S. Cl. .................................... 422/300; 53/426
(58) Field of Classification Search .............. 422/300; 53/426
See application file for complete search history.

(56) References Cited

U.S. PATENT DOCUMENTS

| | | | |
|---|---|---|---|
| 4,120,134 A | 10/1978 | Scholle | |
| 4,458,734 A | 7/1984 | Scholle et al. | |
| 4,498,508 A | 2/1985 | Scholle et al. | |
| 5,007,232 A * | 4/1991 | Caudill | .......................... 53/426 |
| 5,128,101 A | 7/1992 | Boynton | |
| 5,167,140 A * | 12/1992 | Cooper et al. | ................ 73/40.7 |
| 5,173,259 A | 12/1992 | Bordini | |
| 6,148,874 A | 11/2000 | Rutter et al. | |
| 6,209,591 B1 | 4/2001 | Taggart | |
| 6,330,780 B1 | 12/2001 | Shipway | |
| 6,622,457 B2 | 9/2003 | Kurth | |
| 6,969,012 B2 * | 11/2005 | Kangas et al. | ................ 239/400 |
| 2004/0228759 A1 | 11/2004 | Frost | |
| 2008/0089794 A1 * | 4/2008 | Okumura et al. | ............ 417/395 |

FOREIGN PATENT DOCUMENTS

| | | | |
|---|---|---|---|
| DE | 2507790 | | 5/1976 |
| GB | 1513266 | * | 6/1978 |
| JP | 407101426 | | 4/1995 |

* cited by examiner

*Primary Examiner*—Sean E Conley
*Assistant Examiner*—Kevin C Joyner
(74) *Attorney, Agent, or Firm*—Jovan N. Jovanovic; Vladan M. Vasiljevic; The Watson I.P. Group, PLC

(57) ABSTRACT

A sterilization system for use in association with a filler device configured for filling at least one of rigid and flexible containers comprising a sterilization chamber and a sterilant supply assembly. The sterilization chamber includes a housing, an inlet into the housing, an outlet from the housing and a product retainer assembly. These components define a cavity within which to position a portion of a fitment. The sterilant supply assembly comprises a steam generating system having a steam supply conduit extending therefrom and a joint mixing conduit coupled with the inlet into the housing of the sterilization chamber, a hydrogen peroxide storing system and a member for metering liquid phase hydrogen peroxide from the hydrogen peroxide storing system into the steam supply conduit for mixing therewith, and, in turn, introduction thereof into the cavity of the sterilization chamber.

8 Claims, 4 Drawing Sheets

STERILIZATION SYSTEM AND METHOD SUITABLE FOR USE IN ASSOCIATION WITH FILLER DEVICES

BACKGROUND OF THE INVENTION

1. Field of the Invention

The invention relates in general to sterilization systems, and more particularly, to a sterilization system which is suitable for the sterilization of rigid containers and flexible bags and which uses steam combined with hydrogen peroxide injection.

2. Background Art

Sterilization chambers and sterilization processes are well known in the art. Such processes associated with container filling are shown in U.S. Pat. No. 4,458,734 issued to Scholle et al and in U.S. Pat. No. 4,498,508 issued to Scholle et al. The entire specification of these two patents is hereby incorporated by reference. These references disclose the use of dry heat to sterilize various components during the filling process.

The use of steam as a sterilant for sterilizing portions of containers prior to filling is well known in the art. Similarly, the utilization of hydrogen peroxide as a sterilant for sterilizing portions of containers prior to filling is likewise known in the art. One known method of sterilization is through the use of a superheated steam. While such a system does not require any chemicals and the sterilant is widely available, the temperatures required to effectively sterilize a surface, and the dwell time associated with an effective sterilization can often be excessive.

Another method of sterilizing is by applying liquid hydrogen peroxide on an object to be sterilized then applying steam onto the object to be sterilized. Advantageously, such a procedure can be accomplished with lower temperatures, however, the time needed to effect proper sterilization is often not reduced as compared to the utilization of steam alone. Additionally, such systems may expose the operator to unacceptable levels of hydrogen peroxide.

Yet another method of sterilizing can be achieved by applying hydrogen peroxide in liquid form to a heated surface proximate the object to be sterilized. Advantageously, this procedure does not require steam. Such a system generally requires tight controls and can be hazardous to operators which may be exposed to unsuitable levels of hydrogen peroxide.

It is an object of the present invention to introduce hydrogen peroxide in liquid phase into a steam conduit prior to introduction of same into a sterilization chamber.

It is another object of the present invention to reduce the temperatures and the dwell times necessary for effective sterilization of a fitment of a container.

It is another object of the invention to minimize user exposure to elevated levels of hydrogen peroxide.

These objects as well as other objects of the present invention will become apparent in light of the present specification, claims, and drawings.

SUMMARY OF THE INVENTION

The invention is directed to a sterilization system for use in association with a filler device configured for filling at least one of rigid and flexible containers. The system comprises a sterilization chamber and a sterilant supply assembly. The sterilization chamber includes a housing, an inlet into the housing, an outlet from the housing and a product retainer assembly. These components define a cavity within which to position a portion of a fitment. The sterilant supply assembly comprises a steam generating system, a hydrogen peroxide storing system and means for metering liquid phase hydrogen peroxide. The steam generating system has a steam supply conduit extending therefrom and a joint mixing conduit coupled with the inlet into the housing of the sterilization chamber. The metering means is configured for metering liquid phase hydrogen peroxide from the hydrogen peroxide storing system into the steam supply conduit for mixing therewith, and, in turn, introduction thereof into the cavity of the sterilization chamber.

In a preferred embodiment, the sterilization system further comprises means for isolating the metering means from the steam, so as to preclude undesirable temperature elevation within the metering means.

In one such embodiment, the isolating means comprises a translating assembly configured for selectively placing the injector in fluid communication with the joint mixing conduit. Preferably, the translating assembly includes an actuator coupled to the metering means.

In another such preferred embodiment, the translating assembly further includes a recovery assembly surrounding at least a portion of the metering means, to, in turn, preclude the undesirable release of hydrogen peroxide from the injector upon movement thereof by the translating assembly.

In yet another preferred embodiment, the isolating means comprises a cooling assembly surrounding at least a portion of the metering means proximate the joint mixing conduit. The cooling assembly may include means for directing air therethrough.

Alternatively, the cooling assembly may include means for directing fluid therethrough.

In a preferred embodiment, the hydrogen peroxide metering means comprises an injector. Preferably, the injector is electronically controlled.

In a preferred embodiment, the metering means includes means for injecting a predetermined amount of hydrogen peroxide a predetermined intervals.

In another preferred embodiment, the sterilization system further comprises a recovery system comprising a conduit and a tank. The conduit is coupled to the outlet of the housing. The tank coupled to the conduit.

In yet another preferred embodiment, the hydrogen stored within the hydrogen peroxide storing system is a solution of approximately 35% hydrogen peroxide.

In a preferred embodiment, the steam is at a temperature of less than 250° F. and a dwell time for the steam against a cap (fitment) is less than four seconds, and preferably less than three seconds.

In another aspect of the invention, the invention comprises a method of sterilization utilized in association with a filler device, comprising the steps of: introducing at least a portion of a fitment into a cavity of a sterilization chamber; directing steam in a conduit toward cavity of the sterilization chamber; injecting hydrogen peroxide in liquid phase into the steam within the conduit; mixing the hydrogen peroxide with the steam; and directing the mixed hydrogen peroxide and steam into the cavity.

In a preferred embodiment, the method further comprises the step of isolating the hydrogen peroxide from the heat of the steam prior to injection of the hydrogen peroxide into the steam.

In one such embodiment, the step of isolating further comprise the step of selectively placing a hydrogen peroxide injector in fluid communication with the conduit.

In another such embodiment, the step of isolating further comprises the step of cooling a hydrogen peroxide injector.

In one preferred embodiment, the step of injecting comprises the step of intermittently directing a quantity of hydrogen peroxide into conduit.

In another preferred embodiment, the method further includes the steps of stopping the step of injecting; and stopping the step of directing after stopping the step of injecting for a predetermined period of time.

In one preferred embodiment, the method further comprises the step of removing the portion of the fitment from the sterilization chamber.

In another preferred embodiment, the step of introducing comprises the steps of: coupling the fitment within a product retainer assembly; and positioning a housing of the sterilization chamber over at least a portion of the fitment so as to position same within the cavity.

BRIEF DESCRIPTION OF THE DRAWINGS

The invention will now be described with reference to the drawings wherein.

DETAILED DESCRIPTION OF THE INVENTION

Figure 1:
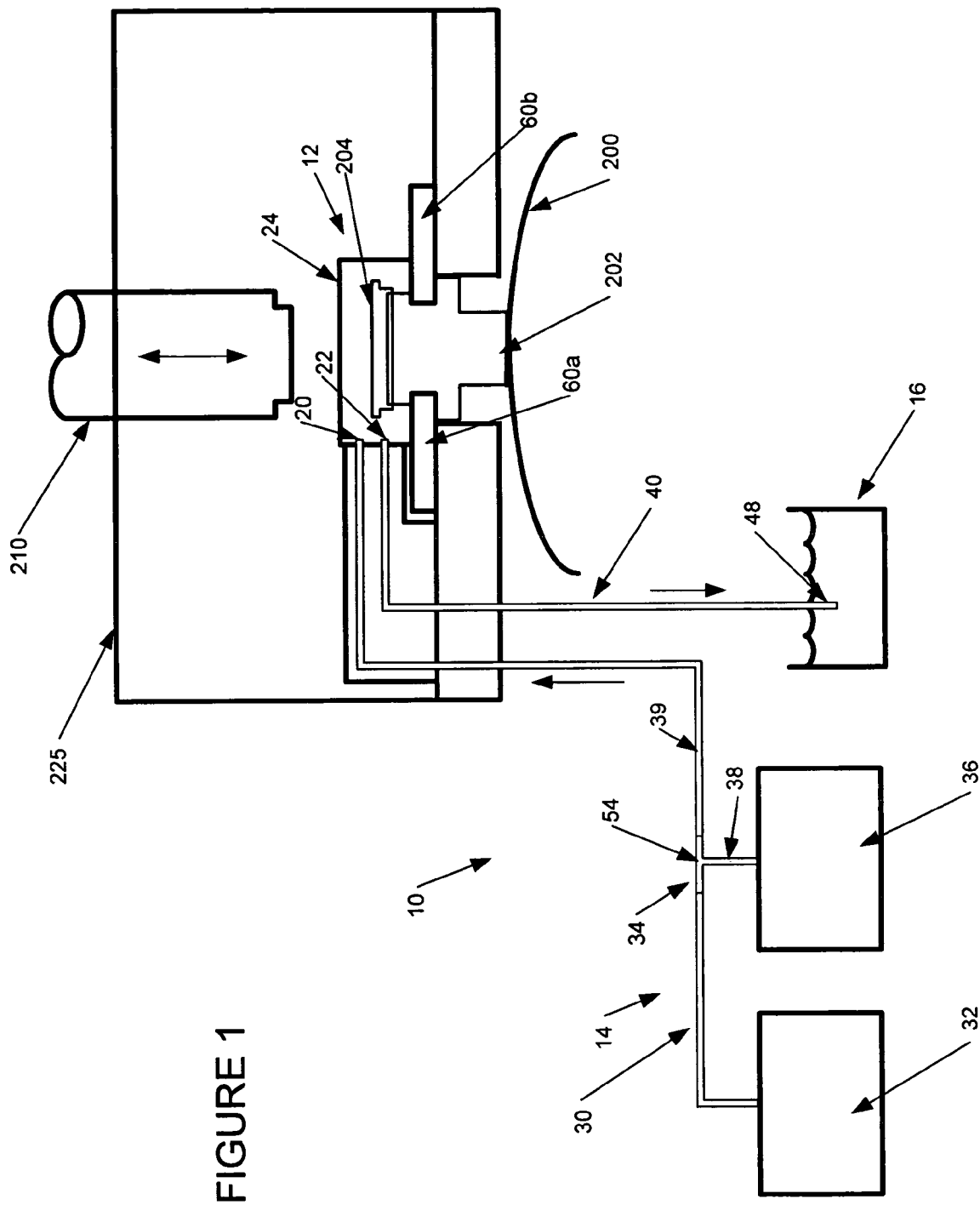
FIG. 1 of the drawings is a schematic representation of an embodiment of the present sterilization system.

While this invention is susceptible of embodiment in many different forms, there is shown in the drawings and described herein in detail a specific embodiment with the understanding that the present disclosure is to be considered as an exemplification of the principles of the invention and is not intended to limit the invention to the embodiment illustrated.

It will be understood that like or analogous elements and/or components, referred to herein, may be identified throughout the drawings by like reference characters. In addition, it will be understood that the drawings are merely schematic representations of the invention, and some of the components may have been distorted from actual scale for purposes of pictorial clarity.

Referring now to the drawings and in particular to FIG. 1, sterilization system is shown generally at 10. System 10 is suitable for use in association with filler devices. The filler devices are generally suitable for the filling of flexible bags and rigid containers. It is contemplated that the system may be applicable to new equipment as well as retrofittable on existing equipment. In many such systems, a fitment is introduced into the system within a larger housing 225, sterilized and subsequently filled with a flowable material through filler valve 210. Once filled it is released.

The sterilization system 10 comprises sterilization chamber 12, sterilant supply assembly 14 and recovery system 16. The sterilization chamber 12 includes inlet 20, outlet 22, housing 24 and product retainer assembly 26. In certain embodiments, the sterilization chamber may commonly be referred to as a sterilization cup or steam cup. Housing 24 defines cavity 28 which is sized to readily accept a fitment of a rigid or flexible container, such fitments typically include spout 202 of container 200 and cap 204. It will be understood that the fitment may comprise any combination of the spout, the cap, or dispensing elements coupled to the spout. Inlet 20 provides ingress into cavity 28. Outlet 22 provides egress from cavity 28. The inlet and outlet are positioned in such a manner that allows for the proper circulation and direction of the sterilant throughout the cavity in an effort to maximize the efficacy of the sterilant on the fitment that is positioned within the cavity.

In certain embodiments, as is shown in FIG. 1, a filler head and an uncapper/recapper can be maintained within the larger housing so that once the container is positioned such that the fitment is retained, a portion thereof is sterilized, the cap is removed, the container is filled with a flowable material and the cap is replaced prior to removal of the container from the larger housing. In other embodiments, the sterilization chamber can be withdrawn, and the container can proceed to different stations (linearly or rotatively) for capping, uncapping and filling. In the embodiment shown, it is contemplated that portions of the fitment remains within the larger housing for the filling procedure.

Figure 3B:
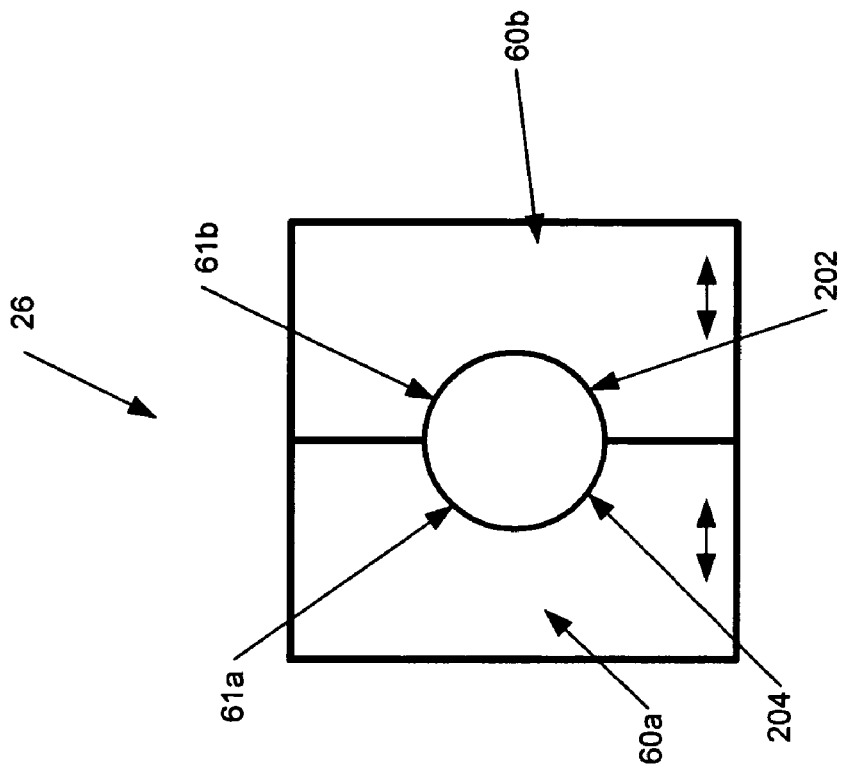
FIGS. 3a and 3b of the drawings are each a schematic top plan view of an embodiment of the product retainer assembly of the present invention showing both a released position wherein a fitment is not captured thereby and a retained position wherein a fitment is captured thereby.
Figure 3A:
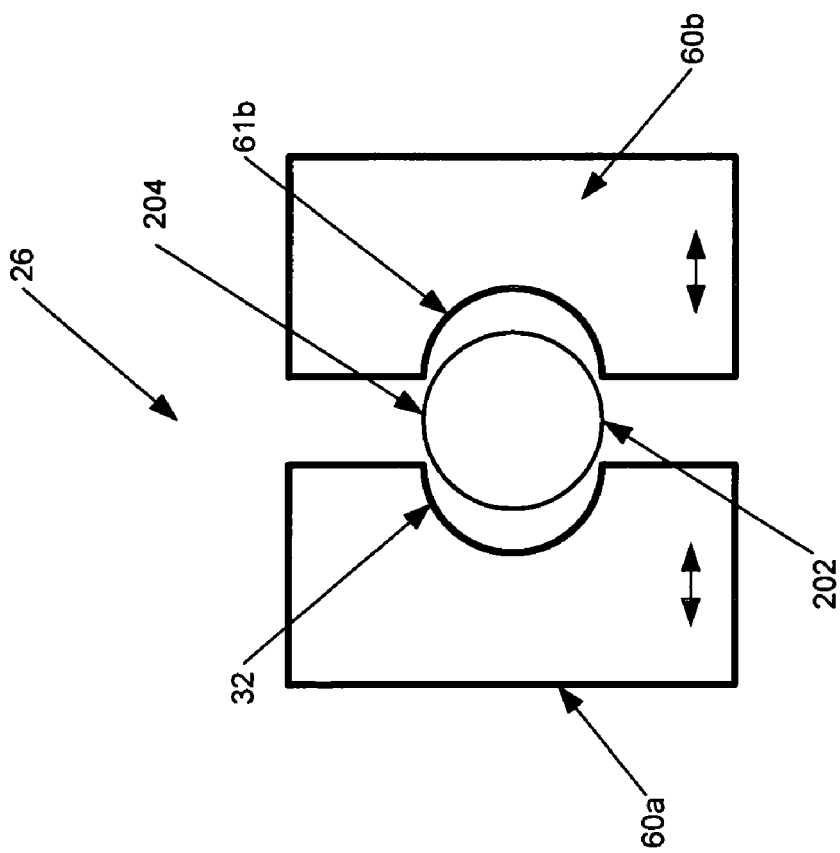

Product retainer assembly 26 is shown in FIGS. 3a and 3b as comprising a pair of opposing horizontal plates 60a, 60b. Each plate includes void 61a, 61b, respectively. The voids are configured to receive portions of the fitment within voids 61a, 61b, when the opposing horizontal plates are placed in an abutting relationship. The plates can be spread apart to release or to receive the fitment. Of course, in other embodiments, the product retainer assembly may comprise any number of different structures, such as, for example jaw members that pivot about one or more axis of rotation. Indeed, the invention is not limited to any particular manner in which to releasably retain spout 202.

Sterilant supply assembly 14 is shown in FIG. 1 as comprising steam supply conduit 30, steam generating system 32, peroxide conduit 34, peroxide storing system 36, means 38 for metering peroxide, and joint mixing conduit 39. Steam supply conduit 30 extends from the steam generating system 32 toward the item to be sterilized. The steam generating system 32 can be any number of different systems which generates steam at temperatures of as high as 350° F. Preferably, the steam is at approximately 60 psi and at a temperature of 290° F. It will be understood that the higher the temperature and pressure of the steam the harsher the environment for the device components and the container components. Of course, the invention is not limited to a particular temperature for the steam, and certain exemplary temperatures and pressures are set forth below. The supply conduit is of sufficient strength to carry the steam at elevated temperatures and pressures.

Peroxide storing system 36 is shown in FIG. 1 as comprising a tank capable of storing a hydrogen peroxide solution in liquid phase at a predetermined concentration. In certain embodiments the concentration of hydrogen peroxide may be between 20% and 50% concentration, preferably approximately 35% concentration. Other concentrations are likewise contemplated. Generally, the hydrogen peroxide is provided in a generated state. It is contemplated that the hydrogen peroxide can be generated by the system, however, due to the volatility of hydrogen peroxide in certain concentrations, hydrogen peroxide is preferably generated elsewhere and provided to the system in a generated state.

Hydrogen peroxide metering means 38 is shown in FIG. 1 as comprising injector 54 which can be selectively activated, and means 55 for isolating the injector from the heat transferred from the steam to the various components. The injector is capable of injecting a predetermined quantity of hydrogen peroxide in the liquid phase into the hydrogen peroxide conduit at a predetermined time. The injector may comprise a pneumatic positive displacement device which can be controlled electronically or otherwise by the system that operates the filler device, or a dedicated system which controls the sterilization system. Of course, other means for metering, such as mechanically actuated valves and the like are also contemplated.

As the hydrogen peroxide is injected into the steam in a liquid state, the temperature of the various steam carrying or contacting will rise due to the exposure to the elevated steam temperatures. By limiting the size cross-sectional configuration of the hydrogen peroxide conduit, the hydrogen peroxide that is injected into the steam remains predominantly in a liquid state, rather than becoming a gas. As set forth above, it is desirable to inject hydrogen peroxide in a liquid state.

In certain embodiments, heat isolation means 55 may be employed. The Heat isolation means precludes an undesirable change in the operating temperature proximate the hydrogen peroxide injector 54 so that the hydrogen peroxide does not undesirably increase in temperature. An undesirable increase in temperature can initiate a local or more widespread phase change in the hydrogen peroxide prior to injection.

Figure 4B:
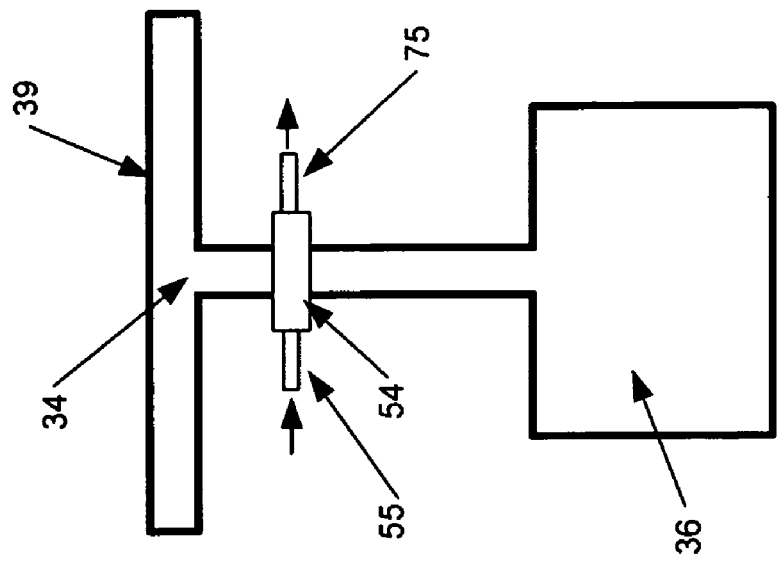
FIGS. 4a and 4b of the drawings are each schematic representations of the means for isolating the hydrogen peroxide injector from the heat generated by the steam, so as to preclude undesirable temperature levels within the hydrogen peroxide prior to injection.
Figure 4A:
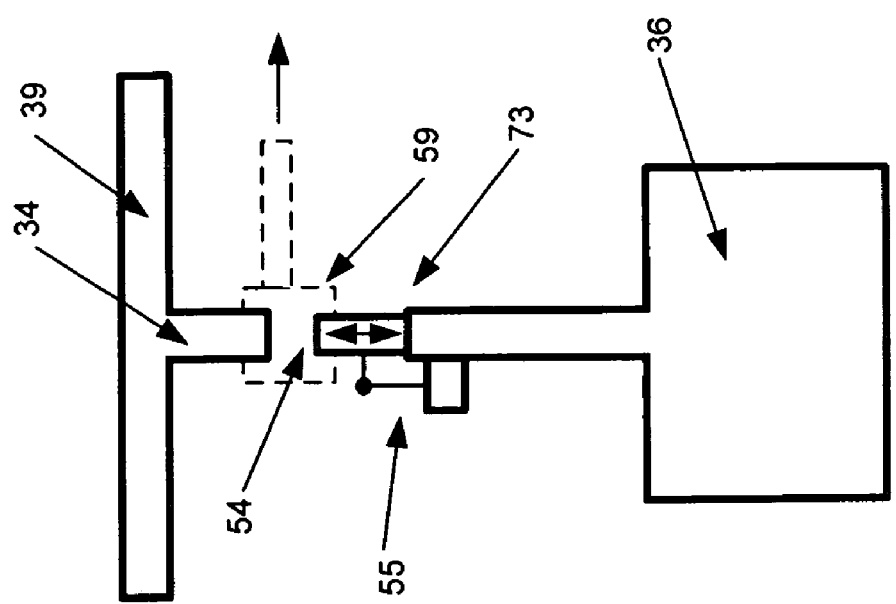

With reference to FIG. 4a, the heat isolation means 55 may comprise a translating assembly 73 which can selectively place the injector 54 into contact with the joint mixing conduit when the injector 54 is to inject hydrogen peroxide into the joint mixing conduit. The translating assembly 73 can then withdraw the injector when between injection cycles. As such, the injector can be isolated from the heat generated by the steam, and can be introduced for relatively short periods of time when necessary.

The translating assembly includes actuator 60 which electronically, mechanically or through hydraulic means translates the injector as desired. For example, actuator 60 may comprise a solenoid that can be electrically actuated to move the injector in response to electrical signals. In another embodiment, the actuator may include an air cylinder or pair of air cylinders that can selectively place the injector in fluid communication with the joint mixing conduit.

To preclude any undesired leaking or escape of hydrogen peroxide due to the movement of the injector 54, recovery assembly 59 may be employed. Specifically, the recovery assembly may comprise an encasement system which can apply a vacuum as the injector is placed in fluid communication or released form fluid communication with the joint mixing conduit. As such, any hydrogen peroxide that may be released due to the joining or separation of the injector from the joint mixing conduit can be captured by the encasement system and directed to recovery system 16.

In another embodiment, shown in FIG. 4b, the heat isolation means 55 may comprise a cooling assembly 75 which cools at least the immediate area of injector 54 to an extent sufficient to preclude the undesired elevation in temperature of the peroxide prior to injection thereof into the steam. The cooling assembly may comprise a heat exchanger that relies on a flowing fluid to withdraw heat from the area surrounding the injector. For example, the fluid may comprise air which is directed beyond the injector at a predetermined or otherwise desired flow rate and temperature. In other embodiments, the fluid may comprise a liquid, such as water or a glycol based fluid which is circulated beyond the injector at predetermined temperatures and flow rates.

Of course the heat isolation means may comprise other variations of the foregoing. For example, insulation may be utilized between the injector 54 and the joint mixing conduit to insulate the injector from the heat of the steam. Moreover, various combinations of the foregoing systems may be utilized to achieve the same result.

The joint mixing conduit 39 directs steam, and when injected, hydrogen peroxide from the respective conduits 30, 34 to inlet 20 of the sterilization chamber 12. The joint mixing conduit may be of a number of different configurations. The position and angle at which the conduit 39 connects with inlet 20 can be varied to achieve the proper distribution and flow through the sterilization chamber. It will be understood that a single conduit may be supplied wherein the steam conduit, the joint mixing conduit and the hydrogen peroxide conduit comprise regions of a single integrated conduit.

Recovery system 16 is shown in FIG. 1 as comprising conduit 40 and tank 42. Conduit 40 is coupled to outlet 22 of the sterilization chamber and directs the sterilization fluids away from the sterilization chamber to the recovery tank 42. Tank 42 facilitates the recovery of the fluid utilized for sterilization. The tank recovers the water and the hydrogen peroxide that has passed through the sterilization chamber. Indeed, as the system is closed, the tank recovers virtually all of the fluids that pass through the sterilization chamber. As such, an operator of such a closed system is not exposed to increased levels of hydrogen peroxide during the operation thereof.

Once filled, the tank can be emptied. Inasmuch as the hydrogen peroxide is vaporized in the process and effectively breaks down to water, tank 42 includes predominantly water. The water can be reused or otherwise disposed. In certain embodiments, filtration or other purification can take place prior to the redirection into the steam generating system.

Figure 2:
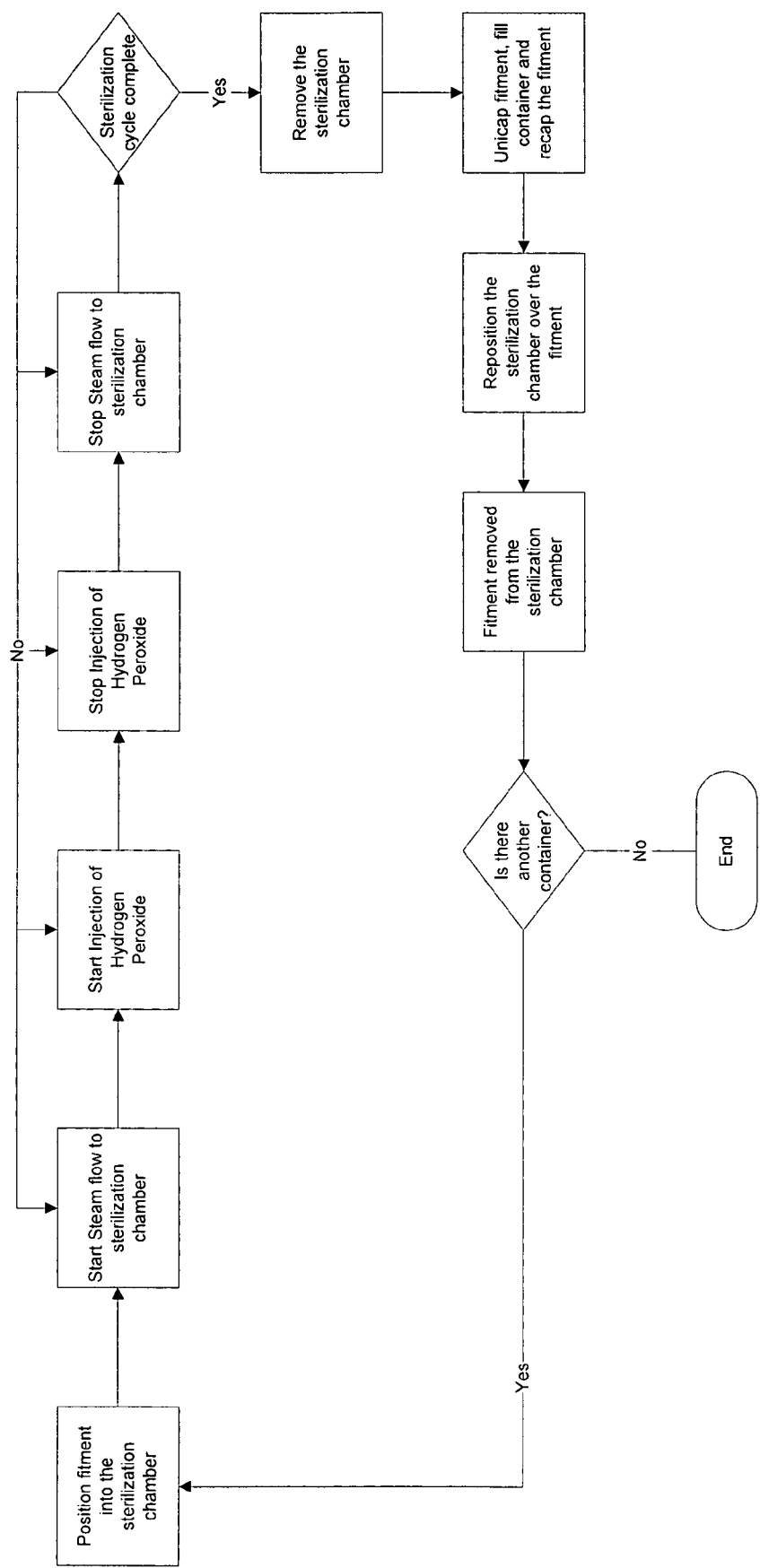
FIG. 2 of the drawings is a schematic representation of the operation of an embodiment of a method of sterilization suitable for filler devices.

One preferred method of operation is shown in FIG. 2. In particular steam is generated in the steam generating system 32. Similarly, hydrogen peroxide of the desired concentration is paced in the hydrogen peroxide storing system 36. Next, container 200 having a fitment is introduced into the sterilization chamber. Specifically, and as described with reference to FIGS. 3a and 3b, the horizontal plates 60a, 60b cooperate to retain the spout within the voids 61a, 61b. In such a configuration, a portion of the spout 202 and cap 204 (i.e., the fitment) are positioned within cavity 28. The inlet 20 and outlet 22 provide a passageway for the sterilant.

The flow of steam is next initiated. The steam flows through steam supply conduit 30 through joint mixing conduit 39, through inlet 20 into cavity 28. Once in cavity 28, contact is made with the fitment. One of skill in the art can geometrically configure the inside of the sterilization chamber so as to create the desired flow pattern around the fitment to effectively direct the steam flow at the desired areas.

As the steam is directed into the sterilization chamber, the means 38 for metering hydrogen peroxide meters predetermined amounts of liquid phase hydrogen peroxide solution from the liquid phase hydrogen peroxide storing system 36 into the hydrogen peroxide conduit to joint mixing conduit 39. The timing and the quantity of hydrogen peroxide that is transmitted can be varied depending on the application. In one embodiment, 0.1 cubic centimeter (cc) can be injected every half second by injector 54. In another embodiment, a single 0.6 cc injection is injected for the sterilization of a cap. Of course, such quantities and timing can be varied. Advantageously, in the presence of steam, the liquid phase hydrogen peroxide changes phase quickly after introduction into the joint mixing conduit. The phase change leads to rapid expansion.

To preclude an undesirable elevation in temperature of the peroxide prior to injection by the injector 54, heat isolation means 55 may be employed. In the embodiment of FIG. 4(a), the injector 54 can be placed in fluid communication with the joint mixing conduit for each injection for a cycle of injections necessary to sterilize one or items positioned in the sterilization chamber. The timing of the movement of injector 54 can be determined by evaluating the temperature rise in injector 54 as a function of contact time with the joint mixing conduit.

In the embodiment of FIG. 4b, injector 54 can be cooled by cooling assembly 75 of the heat isolation means. In such an embodiment, the cooling fluid can be directed beyond the injector so as to maintain a desired temperature range. Indeed, it is contemplated that a flow rates, temperatures and fluids can be varied so as to achieve the desired operating temperature of injector 54.

The hydrogen peroxide metering continues for a predetermined period of time. After the predetermined number of injections of liquid phase hydrogen peroxide have been made into joint mixing conduit, the steam preferably continues for a predetermined period of time. As such, near the end of the cycle, only steam is directed through the sterilization chamber. Such a configuration is useful for purging the sterilization chamber of any residual hydrogen peroxide prior to release of the fitment. The quantity of peroxide, the injection parameters, the temperature and pressure of the steam and the duration of the cycle can be varied. Certain parameters that have been contemplated are set forth below in the comparative data.

As the steam and hydrogen peroxide pass through the sterilization chamber, eventually, the gas is directed through outlet 22 and into conduit 40 of the recovery system. Continued flow directs the sterilant to tank 42. On the way to the tank and in the tank, the hydrogen peroxide breaks down into water an oxygen gas. In certain embodiments, a filtration unit may be utilized to filter the dead microbes that were effectively killed by the procedure.

Once the sterilization procedure has been completed, the sterilization chamber may include an uncapper (not shown) which can uncap the container prior to moving away from the spout. Next, a fill valve, such as fill valve 210 can be placed into the proper position and the container can be filled with product. Once filled, the sterilization chamber can return and the capper can recap the container. The container can then be released by the product retainer assembly.

After release of the container by the product retainer assembly, the cycle can be repeated with a second container. Specifically, the new container is retained within the sterilization chamber and the sterilization process is repeated (as well as the fill procedure).

A test system was assembled to test the efficacy of the present invention as compared to conventional steam and hydrogen peroxide systems. The test system included the following parameters. In particular, spores of *Geobacillus stearothermophilus* were prepared in sterile deionized water. These spores were spot inoculated onto a particular type of fitment in two locations. The particular fitment was the 800 FT fitment of Scholle Corporation, which is the subject of U.S. Patent Publication No. 2006/0043113 A1 entitled "Cap Assembly and Container used therewith," the entire specification of which is hereby incorporated by reference. An exemplary tap is shown in FIG. 2 of the publication.

The first location of inoculation was in the trench formed by the cover and the valley of the fitment, at a concentration of 1.7×106 CFU/spot. The second location of inoculation was on the annular rim (or skirt) and in alignment with the inoculation in the trench, and was at a concentration of 1.7×105 CFU/spot. The spores were allowed to dry on the cap before placing in individual sterile whirl-pak bags.

Various taps were then processed in accordance with the present invention. A number of fitments were processed at different temperatures and different injections of liquid phase hydrogen peroxide. Additionally, several tests were run wherein no liquid phase hydrogen peroxide was utilized (i.e., a conventional sterilization process).

The processed fitments were then analyzed to determine which of the processed taps were successful in killing the spores that were placed onto the fitments. In particular, each inoculum site was swabbed separately with a sterile cotton swab pre-moistened with Dextrose Tryptone Broth with 1% yeast extract (DTB+ye). The swab was then cultured in a 10 ml tube of DTB+ye and incubated for 14 days at 55° C. After fourteen (14) days, the tubes were read after the 14 days. A sample was considered positive if turbidity was present and the broth color changed from purple to bright yellow, indicating growth of the test organism.

At a 300° F. temperature for three 0.5 second cycles utilizing no injection of hydrogen peroxide, all eight of the test samples showed a positive result for spores in the trench, and one of the eight fitments showed a positive result for spores in the skirt. On the other hand, at temperatures of 280° F. and 240° F. and for one 1.5 second cycle with injections of 0.6 cc, 0.8 cc, and 1.0 cc resulted in not a single of the thirty test samples showed a positive result for spores in the trench or on the skirt. As will be understood, both the total treatment time and the temperatures were lower for the samples that were injected with hydrogen peroxide.

From the test results it has been determined that due to the increased effectiveness of the present system, the time necessary to sterilize a fitment can be greatly reduced, while at the same time reducing the steam temperature required for effective sterilization. In fact, at a temperature below 250° F., and preferably below 240° F., fitments can be fully sterilized in less than 4 seconds, and preferably less than 3 seconds, of steam/peroxide exposure.

The foregoing description merely explains and illustrates the invention and the invention is not limited thereto except insofar as the appended claims are so limited, as those skilled in the art who have the disclosure before them will be able to make modifications without departing from the scope of the invention.

What is claimed is:

1. A sterilization system for use in association with a filler device configured for filling at least one of rigid and flexible containers comprising:

a sterilization chamber having a housing, an inlet into the housing, an outlet from the housing and a product retainer assembly, thereby defining a cavity within which to position a portion of a fitment; and a sterilant supply assembly comprising a steam generating system having a steam supply conduit extending therefrom and a joint mixing conduit coupled with the inlet into the housing of the sterilization chamber;

a hydrogen peroxide storing system;

means for metering liquid phase hydrogen peroxide from the hydrogen peroxide storing system into the steam supply conduit for mixing therewith, and, in turn, introduction thereof into the cavity of the sterilization chamber, wherein the means for metering comprises an injector; and means for isolating the metering means from the steam supply conduit, so as to preclude undesirable temperature elevation within the metering means, wherein the means for isolating further comprises a translating assembly configured for selectively placing the injector in fluid communication with the joint mixing conduit, and a recovery assembly surrounding at least a portion of the metering means, to, in turn, preclude the undesirable release of hydrogen peroxide from the injector upon movement thereof by the translating assembly.

2. The sterilization system of claim 1, wherein the translating assembly includes an actuator coupled to the metering means.

3. The sterilization system of claim 1 wherein the hydrogen peroxide metering means comprises an injector.

4. The sterilization system of claim 3 wherein the injector is electronically controlled.

5. The sterilization system of claim 1 wherein the metering means includes means for injecting a predetermined amount of hydrogen peroxide a predetermined intervals.

6. The sterilization system of claim 1 further comprising a recovery system comprising:
 a conduit coupled to the outlet of the housing; and
 a tank coupled to the conduit.

7. The sterilization system of claim 1 wherein the hydrogen stored within the hydrogen peroxide storing system is a solution of approximately 35% hydrogen peroxide.

8. The sterilization system of claim 1 wherein the steam is at a temperature of less than 250° F. and a dwell time is less than 4 seconds.

* * * * *